(12) United States Patent
Leiner et al.

(10) Patent No.: US 8,834,158 B2
(45) Date of Patent: Sep. 16, 2014

(54) SCREW SYRINGE AS WELL AS A SYRINGE BARREL AND FEMALE PART FOR A SCREW SYRINGE

(75) Inventors: Uwe Leiner, Midlum (DE); Manfred Thomas Plaumann, Cuxhaven (DE)

(73) Assignee: VOCO GmbH, Cuxhaven (DE)

( * ) Notice: Subject to any disclaimer, the term of this patent is extended or adjusted under 35 U.S.C. 154(b) by 190 days.

(21) Appl. No.: 13/426,405

(22) Filed: Mar. 21, 2012

(65) Prior Publication Data
US 2012/0244493 A1  Sep. 27, 2012

(30) Foreign Application Priority Data

Mar. 22, 2011 (DE) .......................... 10 2011 005 919

(51) Int. Cl.
| | | |
|---|---|---|
| *A61C 5/04* | (2006.01) | |
| *G01F 11/00* | (2006.01) | |
| *A61M 5/315* | (2006.01) | |
| *B65D 83/00* | (2006.01) | |
| *B05C 17/01* | (2006.01) | |
| *A61C 5/06* | (2006.01) | |
| *A61M 5/31* | (2006.01) | |

(52) U.S. Cl.
CPC ............ *A61C 5/062* (2013.01); *A61M 5/31583* (2013.01); *B65D 83/0011* (2013.01); *A61M 5/31586* (2013.01); *B05C 17/0133* (2013.01); *A61M 5/3135* (2013.01)
USPC .............................. 433/90; 222/390; 604/224

(58) Field of Classification Search
USPC ........ 433/80, 89–90; 604/224, 227, 218, 220, 604/187, 207, 208, 211, 92–94, 122, 222; 222/390
See application file for complete search history.

(56) References Cited

U.S. PATENT DOCUMENTS

| | | | | |
|---|---|---|---|---|
| 4,198,756 A | * | 4/1980 | Dragan | 222/326 |
| 5,618,273 A | * | 4/1997 | Fischer | 604/211 |
| 5,647,856 A | | 7/1997 | Eykmann et al. | |

(Continued)

FOREIGN PATENT DOCUMENTS

| | | |
|---|---|---|
| DE | 3129348 | 2/1983 |
| DE | 8805104 | 6/1988 |

(Continued)

OTHER PUBLICATIONS

"Inclined." Merriam-Webster.com. Merriam-Webster, n.d. Web. Mar. 24, 2014. <http://www.merriam-webster.com/dictionary/inclined.*

*Primary Examiner* — Heidi M Eide
(74) *Attorney, Agent, or Firm* — Duane Morris LLP; J. Rodman Steele, Jr.; Gregory M. Lefkowitz

(57) ABSTRACT

A screw syringe having a piston spindle with an external thread, a syringe barrel, having a sleeve with a piston end, and a female part with an internal thread is disclosed. The female part slides onto the piston end. The female part has a flange that creates a form fit with a counter-surface at the piston end so axial displacement of the female part in relation to the syringe barrel in the discharge direction is prevented. The female part has retaining surfaces that create a form fit with counter-retaining surfaces of the piston end, thereby preventing axial displacement of the female part in relation to the syringe barrel counter to the discharge direction. The retaining surfaces and counter-retaining surfaces create a form fit that prevents radial relative movement between the retaining surfaces and the counter-retaining surfaces, directed perpendicularly to the sliding direction.

18 Claims, 14 Drawing Sheets

(56) References Cited

U.S. PATENT DOCUMENTS

| | | |
|---|---|---|
| 6,571,992 B2 | 6/2003 | Pierson et al. |
| 6,793,660 B2 | 9/2004 | Kerr et al. |
| 7,270,667 B2 * | 9/2007 | Faccioli et al. ............... 606/94 |
| 7,392,735 B2 * | 7/2008 | Brass et al. ..................... 92/32 |
| 2002/0010431 A1 | 1/2002 | Dixon et al. |
| 2006/0131344 A1 | 6/2006 | Brass |
| 2011/0125088 A1 | 5/2011 | Dixon et al. |
| 2013/0043282 A1 * | 2/2013 | Niklasson ................... 222/390 |

FOREIGN PATENT DOCUMENTS

| | | |
|---|---|---|
| DE | 19833238 | 12/1999 |
| GB | 1515219 | 6/1978 |
| WO | 0193787 | 12/2001 |

* cited by examiner

SCREW SYRINGE AS WELL AS A SYRINGE BARREL AND FEMALE PART FOR A SCREW SYRINGE

CROSS-REFERENCE TO RELATED APPLICATIONS

This application claims the benefit of German Patent Application No. 10 2011 005 919.9 filed Mar. 22, 2011, which is incorporated herein by reference in its entirety.

FIELD OF THE INVENTION

The invention relates to a screw syringe for dispensing a material, in particular a pasty and/or flowable dental substance, comprising a piston spindle with an external thread, a syringe barrel with a longitudinal axis, comprising a sleeve for containing a material, wherein the sleeve has a discharge end for discharging a material contained in the sleeve in an axial discharge direction and a piston end for accommodating the piston spindle, and a female part with an internal thread for engaging with the external thread of the piston spindle, wherein the female part is slid in a radial sliding direction onto the piston end of the syringe barrel.

The invention also relates to a syringe barrel for a screw syringe for dispensing a material of the type mentioned above, comprising a sleeve for containing a material, wherein the sleeve has a discharge end for discharging a material contained in the sleeve in an axial direction and a piston end for accommodating a piston spindle, and wherein the piston end is designed in such a way that a female part for a screw syringe of the type mentioned above can be slid in a radial sliding direction onto the piston end.

The invention also relates to a female part for a screw syringe for dispensing a material of the type mentioned above, comprising an internal thread for engaging with an external thread of a piston spindle, wherein the female part is designed in such a way that it can be slid in a radial sliding direction onto a piston end of a syringe barrel for a screw syringe of the type mentioned above.

BACKGROUND OF THE INVENTION

Screw syringes of the type mentioned above are used for dispensing, in particular dosed dispensing, of a material. The materials concerned are in particular (but not exclusively) flowable and/or pasty dental substances or dental materials. In dentistry different materials are used in various applications. An example of these is tooth-coloring plastic filling materials with a plastic matrix and fillers, known as composites. Composites can have a highly viscous, packable consistency or a low-viscosity, flowable consistency.

Dental materials such as composites are normally sold in pre-filled screw syringes. Such a pre-filled syringe contains the material to be dispensed in a sleeve of the syringe barrel with a preferably partially or completely hollow cylindrical form. By operating the piston spindle the material is pushed out of the discharge end of the sleeve in an axial discharge direction, in that when the piston spindle is rotated by engaging the external thread of the piston spindle with the internal thread of the female part the piston spindle advances into the sleeve filled with material of the syringe barrel and thus expels the material from the sleeve.

In other application areas flowable and/or pasty materials may also be dispensed from a screw syringe, for example in welding, when applying pastes or in the application of adhesives or sealants.

In order to be able to drive the piston spindle in the sleeve of the syringe barrel in the axial discharge direction, the internal thread of the female part must have a smaller diameter than the sleeve of the syringe barrel. The female part with the internal thread must therefore be applied to or mounted on the syringe barrel. A screw connection between the female part and the syringe barrel has the disadvantage that when operating the piston spindle the screw connection between the syringe barrel and the female part can be unintentionally released.

Another possible connection can be achieved by a coupling mechanism in which the female part is slid in a radial sliding direction onto the piston end of the syringe barrel. Here the piston end of the syringe barrel refers to a section at the end of the syringe barrel into which the piston spindle penetrates, that is to say an area at the end of the syringe barrel that faces the discharge end of the sleeve. Screw syringes with a coupling mechanism can still be improved upon, however, in particular with regard to the reliability of the connection between the female part and the syringe barrel and with regard to simplification of the assembly process.

SUMMARY OF THE INVENTION

An object of the invention is to indicate a screw syringe and a syringe barrel as well as a female part for a screw syringe, which compared to known screw syringes have an improved coupling mechanism or components for such a coupling mechanism. A further object of the invention is to indicate a screw syringe and a syringe barrel, and a female part for a screw syringe, which prevent or make more difficult an unintentional release of the connection between the female part and the syringe barrel and/or an unintentional deformation of one or a plurality of parts of the screw syringe, in particular of the female part. A further object of the invention is to indicate a screw syringe and a syringe barrel, and a female part for a screw syringe, which offer improvements in terms of hygiene aspects. A further object of the invention is to indicate a screw syringe and a syringe barrel, and a female part for a screw syringe, with simpler or improved handling. A further object is to simplify the assembly process. Another problem for the invention is to indicate a screw syringe and a syringe barrel, and a female part for a screw syringe, that guarantee a reliable securing of the female part to the syringe barrel.

The object is achieved by a screw syringe for dispensing a material, in particular a pasty and/or flowable dental substance, comprising a piston spindle with an external thread, a syringe barrel with a longitudinal axis, comprising a sleeve for containing a material, wherein the sleeve has a discharge end for discharging a material contained in the sleeve in an axial discharge direction and a piston end for accommodating the piston spindle, and a female part with an internal thread for engaging with the external thread of the piston spindle, wherein the female part is slid in a radial sliding direction onto the piston end of the syringe barrel, wherein the female part has a flange, which with a counter-surface at the piston end creates a form fit so that an axial displacement of the female part in relation to the syringe barrel in the discharge direction is prevented, the female part has retaining surfaces, which with counter-retaining surfaces of the piston end create a form fit, so that an axial displacement of the female part in relation to the syringe barrel counter to the discharge direction is prevented, and the retaining surfaces and counter-retaining surfaces create a form fit so that a radial, relative movement between the retaining surfaces and the counter-retaining surfaces, directed perpendicularly to the displacement direction, is prevented.

With a screw syringe according to the invention once it has been slid onto the piston end of the syringe barrel in the axial direction the female part cannot slide in relation to the syringe barrel: an axial displacement of the female part in relation to the syringe barrel in the discharge direction is prevented by a form fit of the flange of the female part with a counter-surface at the piston end and an axial displacement of the female part in relation to the syringe barrel counter to the discharge direction is prevented by a form fit of retaining surfaces formed at the female part with counter-retaining surfaces formed at the piston end. The counter-surface thus provides a stop for the flange, so that the female part cannot be displaced in the discharge direction in relation to the syringe barrel. Similarly the retaining surfaces with the counter-retaining surfaces provide a further stop, preventing a displacement of the female part counter to the discharge direction.

A form fit of a pair of retaining surfaces formed on the female part with a pair of counter-retaining surfaces formed at the piston end is particularly preferable. The retaining surfaces of the female part can preferably be formed at a pair of arms pointing in the axial direction away from the flange of the female part.

With a screw syringe according to the invention following sliding of the female part onto the piston end of the syringe barrel additionally a relative movement between the retaining surfaces and the counter-retaining surfaces in a radial direction, directed perpendicularly to the sliding direction, is prevented by a form fit between the retaining surfaces and the counter-retaining surfaces.

The form fit is preferably primarily effective in the direction perpendicular to the sliding direction and can take various forms, for example retaining surfaces and counter-retaining surfaces formed inclined to the longitudinal axis, curved, undercut and/or stepped.

One advantage of this configuration of the retaining surfaces and counter-retaining surfaces is that as a result of the form fit a radial slipping of the female part from syringe barrel perpendicular to the sliding direction is made more difficult or prevented. In this way a more reliable securing of the female part to the syringe barrel is achieved, in particular also under the effect of the forces, in particular axial forces on the syringe barrel and the female part, applied by operation of the piston spindle for discharging the material contained in the sleeve.

These axial forces are transferred from the spindle via the flange of the female part—and in embodiments in which the retaining surfaces formed at the arms, further via these arms—into the retaining surfaces. In particular in embodiments in which the arms are arranged with a lateral displacement to the retaining surfaces, at this point a moment occurs, that seeks to bend the arms outwards or spread them apart. The configuration of the retaining surfaces and counter-retaining surfaces with a form fit, preventing a radial, relative movement directed perpendicularly to the sliding direction between the retaining surfaces and the counter-retaining surfaces, counteracts this.

In the storage and marketing state the screw syringe preferably has a removable cap with which the discharge end can be sealed until intended use.

The screw syringe according to the invention is preferably manufactured by injection molding, wherein preferably the piston spindle, syringe barrel, female part and optionally cap are produced separately from one another and the female part is slid onto the piston end of the syringe barrel in the radial sliding direction. The piston spindle is screwed into the internal thread of the female part located at the piston end of the syringe barrel only far enough so that in the storage and marketing state a material contained in the sleeve of the syringe barrel is not discharged from the discharge end. Only at the time of intended use of the screw syringe by the user is the piston spindle rotated further into the sleeve and the material contained in the sleeve discharged from the discharge end.

A preferred embodiment is characterized in that the retaining surfaces and counter-retaining surfaces are inclined in relation to the longitudinal axis and/or are undercut, so that a radial, relative movement between the retaining surfaces and the counter-retaining surfaces, directed perpendicularly to the sliding direction, is prevented.

In this embodiment once the female part has been slid onto the piston end of the syringe barrel a relative movement between the retaining surfaces and the counter-retaining surfaces in a radial direction, directed radially to the sliding direction, is prevented in that the retaining surfaces and counter-retaining surfaces are inclined in relation to the longitudinal axis and/or undercut.

It is particularly preferable that the retaining surfaces and counter-retaining surfaces form an angle with the longitudinal axis that is greater than 0° and smaller than 90°. Preferably the angle is in a range with lower limits of 5, 10, 15, 20, 25, 30, 35, 40 or 45° and upper limits preferably of 85, 80, 75, 70, 65, 60, 55, 50 or 45°. An angle of 70° is in particular preferable. The precise choice of angle will be made by a person skilled in the art on the basis of the prevailing material, friction and elasticity parameters of the syringe materials used and on the basis of the geometric spatial considerations associated with the external syringe shape.

An undercut design of the retaining surfaces and counter-retaining surfaces ensures in a particularly reliable and thus advantageous manner security against a radial, relative movement between the retaining surfaces and the counter-retaining surfaces, directed perpendicularly to the sliding direction, and thus reliably prevents the sliding of the retaining surfaces formed on the female part from the counter-retaining surfaces formed at the piston end of the syringe barrel in a radial direction perpendicular to the sliding direction.

A further preferred embodiment is characterized in that the retaining surfaces and counter-retaining surfaces have a stepped design, so that a radial, relative movement between the retaining surfaces and the counter-retaining surfaces, directed perpendicularly to the sliding direction, is prevented.

A form fit in the direction perpendicular to the sliding direction can in particular also be achieved by one or a plurality of stepped, for example right-angled, steps.

In an advantageous embodiment the retaining surfaces and counter-retaining surfaces create a form fit, so that a spreading apart of the female part or parts thereof outwards due to the force applied by operation of the piston spindle is prevented.

When the piston spindle is operated by screwing the external thread of the piston spindle into the internal thread of the female part the piston spindle forces the material contained in the sleeve against a static or sliding friction acting between the inner wall of the sleeve and the material out of the discharge end of the sleeve. In the process an axial force is exerted on the female part and syringe barrel, which in screw syringes with a design not according to the invention can lead to deformation of the female part or parts of this, which can result in a bending up of the female part or parts of this in the direction substantially directed radially outwards. Such a deformation, also referred to as spreading apart, is undesirable, since it can lead to damage of the female part and/or of syringe barrel and/or to a detachment of the connection between the female part and syringe barrel. In the case of retaining and counter-retaining surfaces, which do not create a form fit, the only possibility of preventing slipping is the correspondingly broad design of the retaining and counter-retaining surfaces. This has the disadvantage that the design possibilities for the piston end are severely restricted. In embodiments in which the retaining surfaces and counter-retaining surfaces are formed at the arms, the arms must then be set correspondingly wide apart, as an adverse result of which severe deformations and material stresses of the flange from the impinging forces can be expected.

By a correspondingly designed form fit of the retaining surfaces and counter-retaining surfaces such spreading apart of the female part or parts thereof can be simply and effectively prevented. This is in particular an advantage in embodiments in which the retaining surfaces of the female part are formed at a pair of arms extending outwards in the axial direction from the flange of the female part.

In a preferred embodiment the retaining surfaces and counter-retaining surfaces create a form fit, so that when an axial force is applied by operation of the piston spindle on the retaining surfaces and counter-retaining surfaces force components operate in a direction falling in a plane that is substantially perpendicular to the sliding direction.

With a correspondingly created form fit of the retaining surfaces and counter-retaining surfaces when an axial force is applied to the retaining surfaces and counter-retaining surfaces due to the operation the spindle, force components also operate in a direction falling in a plane positioned perpendicularly to the sliding direction. The force components also operate in particular in a radial direction that is substantially perpendicular to the sliding direction and substantially perpendicular to the longitudinal axis. These force components counteract a radial relative displacement, directed perpendicularly to the sliding direction of the retaining and counter-retaining surfaces, in particular a spreading apart of the female part or parts thereof.

In a preferred embodiment the piston end and the female part in each case have at least one abutting surface, designed and arranged in such as way that in the sliding direction they form a stop for the female part. This type of delimitation of the sliding path offers the advantage, particularly in the case of manual assembly, but also with mechanical assembly of the female part, that sliding on too far and close checking of this are inapplicable.

In this embodiment the abutting surfaces define a position of the female part on the piston end, in which further sliding-on of the female part in the sliding direction is no longer possible, e.g. an end position of the female part on the syringe barrel is defined. Here it is preferable that in this end position the internal thread of the female part is aligned coaxially with the sleeve of the syringe barrel, so that the piston spindle screwed into the internal thread likewise runs coaxially in the sleeve.

The definition of this end position of the female part via the abutting surfaces has the advantage that when the female part is slid onto the syringe barrel the desired end position of the female part can be ensured in a simple manner and sliding beyond the correct position can be effectively prevented by the stop. Similarly a stopping of the sliding process prior to reaching the desired end position of the female part can also be prevented, since as a result of the stop there is no danger of the female part being slid on too far and it can therefore always be slid on as far as the stop.

In a preferred embodiment the piston end and/or the female part has a connection mechanism which prevents or impedes the female part being detached from the piston end counter to the sliding direction.

Such a connection mechanism prevents or impedes the female part being unintentionally slid off from the slid-on position on the piston end of the syringe barrel counter to the sliding direction or being able to be detached from this position counter to the sliding direction. Here the connection mechanism is in particular designed to prevent or impede the detachment of the female part from the syringe barrel counter to the sliding direction by a user with light to normal exertion of force. The connection mechanism according to the invention must not be designed in such a way that detachment counter to the sliding direction is also impossible with considerable application of force. In particular it is preferable that the connection mechanism secures the female part on the piston end in the end position of the female part, defined by the abutting surfaces, and prevents or impedes a detachment from this end position.

In a preferred embodiment the connection mechanism comprises a flange formed on the female part, having an axial latching element that engages with the piston end.

The flange formed on the female part with the axial latching element can be identical to the flange of the female part, creating with a counter-surface on the piston end a form fit, or form a separate, second flange, preferably at an end of the internal thread of the female part facing the abovementioned flange.

An axial latching element is understood to be a latching element having an extension in an axial direction and that serves to create a latched or snap connection between the female part and the piston end when the female part is slid on. In particular it is preferable that the latched or snap connection between the female part and the piston end is created in the end position of the female part, defined by the abutting surfaces.

In a possible further development the latching element takes the form of a protrusion, preferably a wedge.

With this configuration of the latching element when the female part is slid onto the piston end the piston end can be pushed over the protrusion or the wedge and—preferably in the end position of the female part defined by the stop—latch or snap in behind the protrusion or the wedge. Here the protrusion or the wedge has a maximum extension in the axial direction that is dimensioned such that when the female part is slid onto the piston end in the radial sliding direction the piston end slides over the axial protrusion and latches or snaps in behind the axial protrusion.

In a preferred embodiment a wall section of the sleeve is moved back axially on the piston end, wherein this wall section engages with the latching element of the female part.

The extent to which the wall section of the sleeve is moved back axially on the piston end, is preferably matched to the axial extension of the latching element of the female part, in particular a latching element in the form of a protrusion. Amongst others this embodiment has the advantage that the axially moved back wall section of the sleeve can serve for engaging with the latching element of the female part, while the other wall section of the sleeve or at least part thereof can for example as the counter-surface on the piston end create a form fit with a flange of the female part, in order to prevent an axial displacement of the female part in relation to the syringe barrel in the discharge direction.

In a preferred embodiment the piston end and the female part in each case have a cover plate, wherein the cover plates are designed and arranged in such a way that, with the exception of a threaded opening, together they form a substantially enclosed envelope of the piston end and the female part.

By covering the securing mechanism of the piston end and female part once the female part has been slid onto the piston end with cover plates forming a substantially enclosed envelope the susceptibility of the screw syringe to contamination is considerably reduced. The cover plates preferably have substantially smooth surfaces and any gap between the two cover plates is preferably on the one hand kept as small as possible and on the other hand arranged such that the user during normal use does not as a priority touch the syringe in the area of the gap between the cover plates. This is in particular advantageous in areas of application in which the equipment and tools used are subject to strict hygiene requirements, such as for example in dentistry.

In a possible embodiment the cover plates are substantially arranged halves of the screw syringe facing each other in the circumferential direction.

With this embodiment the cover plates are substantially on facing sides of a parting plane that comprises the longitudinal axis. This allows an ergonomic design of the cover plates for gripping by the user.

In an advantageous embodiment the cover plates in each case have a section that is takes the form of part of a hollow cylindrical section and is arranged between two wing grips.

The design of the cover plates with part of a hollow cylindrical section in each case serves to match the cover plates to the preferably hollow sectionally cylindrically shaped piston end of the syringe barrel. The arrangement of two wing grips on either side of each hollow cylindrical section represents an ergonomic design that is easy for the user to grip. This is in particular preferred since the user will normally grip the syringe barrel with the slid-on female part in the area of the wing grips of the cover plates and screw-in the piston spindle with the other hand.

In a further preferred embodiment the abutting surfaces form part of the cover plates.

This ensures that following sliding-on of the female part onto the piston end the gap between the cover plates is as small as possible, since the cover plates serve as abutting surfaces and engage with one another in the end position of the female part on the piston end.

The remaining gaps can also be almost completely sealed by adhesive substances.

In a particularly preferred embodiment the screw syringe takes the following form: a screw syringe for dispensing a material, in particular a pasty and/or flowable dental substance, comprising a piston spindle with an external thread, a syringe barrel with a longitudinal axis, comprising a sleeve for containing a material, wherein the sleeve has a discharge end for dispensing a material contained in the sleeve in an axial discharge direction and a piston end for accommodating the piston spindle, and a female part with an internal thread for engaging with the external thread of the piston spindle, wherein the female part is slid in a radial sliding direction onto the piston end of the syringe barrel, wherein the female part has a flange, that creates a form fit with a counter-surface on the piston end so that an axial displacement of the female part in relation to the syringe barrel in the discharge direction is prevented, the female part has retaining surfaces, which create a form fit with counter-retaining surfaces of the piston end so that an axial displacement of the female part in relation to the syringe barrel counter to the discharge direction is prevented, and the retaining surfaces and counter-retaining surfaces create a form fit so that a radial relative displacement between the retaining surfaces and the counter-retaining surfaces, directed perpendicularly to the sliding direction is prevented, wherein further the piston end and the female part in each case have at least one abutting surface, which is designed and arranged in such a way that in the sliding direction they form a stop for the female part, and the piston end and/or the female part have a connection mechanism, which prevents or impedes the detachment of the female part from the piston end counter to the sliding direction, and the piston end and the female part in each case have a cover plate, wherein the cover plates are designed and arranged in such a way that with the exception of a threaded opening of the female part, together they form a substantially enclosed envelope of the piston end and the female part.

In a further advantageous embodiment the screw syringe comprises a piston tip arranged in the syringe barrel comprising a first section whose external diameter is matched to an internal diameter of the sleeve and which preferably has an indentation for engaging with an end of the piston spindle, wherein the piston tip also preferably comprises a frusto-conical section, which at its tapered end has an external diameter that is smaller than the internal diameter of a discharge opening at the discharge end.

The external diameter of the first section of the piston tip, depending on the material characteristics of the piston tip and sleeve, can be designed to be slightly larger than or the same as the internal diameter of the sleeve, for example if as materials elastically yielding plastics are used. Alternatively the external diameter of the first section of the piston tip can be designed to be slightly smaller than the internal diameter of the sleeve.

The piston tip arranged in the syringe barrel serves to compensate for a possible radial gap between the piston spindle and the inner wall of the sleeve—caused by an external diameter of the piston spindle, that is smaller than the internal diameter of the sleeve—so that when the piston spindle is screwed in, material contained in the sleeve is forced across the full cross-section of the sleeve towards the discharge end. A frusto-conical section of the piston tip, which preferably tapers towards the discharge opening, is then in particular advantageous, if the sleeve of the syringe barrel at the discharge end tapers in a frusto-conical shape, for in this way discharge of the material can be achieved which leaves as little material as possible in the syringe barrel, so that a complete or almost complete discharge of the material from the syringe barrel is possible by operation of the spindle.

The screw syringe according to the invention is preferably operated according to a method for dispensing a material, in particular a pasty and/or flowable dental substance comprising the following steps: provision of a screw syringe according to any one of the abovementioned embodiments and screwing-in of the piston spindle into the internal thread of the female part slid onto the piston end.

According to a further aspect of the invention the object is achieved by a syringe barrel for a screw syringe for dispensing a material according to any one of the embodiments of the screw syringe described above, comprising a sleeve for containing a material, wherein the sleeve has a discharge end for dispensing a material contained in the sleeve in an axial discharge direction and a piston end, and wherein the piston end is designed so that a female part for a screw syringe according to any one of the preceding claims can be slid in a radial sliding direction onto the piston end for accommodating a piston spindle, wherein the piston end has a counter-surface, which can be brought into a form fit with a flange formed on the female part so that a relative axial displacement between the female part and the syringe barrel in the discharge direction is prevented, the piston end has counter-retaining surfaces, which are brought into a form fit with retaining surfaces formed on a female part so that a relative axial displacement between the female part and the syringe barrel counter to the discharge direction is prevented, and the counter-retaining surfaces can be brought into a form fit with the retaining surfaces so that a radial relative displacement between the retaining surfaces and the counter-retaining surfaces, directed perpendicularly to the sliding direction, is prevented.

A preferred embodiment of the syringe barrel is characterized in that the counter-retaining surfaces are inclined to the longitudinal axis and/or undercut, so that a radial relative movement between correspondingly inclined and/or undercut retaining surfaces and the counter-retaining surfaces, directed perpendicularly to the sliding direction, is prevented.

A preferred embodiment of the syringe barrel is characterized in that the counter-retaining surfaces have a stepped design so that a radial relative movement between corresponding retaining surfaces with a stepped design and the counter-retaining surfaces, directed perpendicularly to the sliding direction, is prevented.

A further preferred embodiment of the syringe barrel is characterized in that the counter-retaining surfaces can be brought into a form fit with the retaining surfaces so that a spreading apart of a female part or parts thereof caused by a force applied by operation of a piston spindle is prevented.

A further preferred embodiment of the syringe barrel is characterized in that the counter-retaining surfaces can be brought into a form fit with the retaining surfaces so that when an axial force is applied by the operation of a piston spindle on the counter-retaining surfaces force components act in a direction falling in a plane that is substantially perpendicular to the sliding direction.

A further preferred embodiment of the syringe barrel is characterized in that the piston end has at least one abutting surface, designed and arranged so that in the sliding direction with at least one abutting surface formed at a female part forms a stop for the female part.

A further preferred embodiment of the syringe barrel is characterized in that the piston end has a connection mechanism, which prevents or impedes the detachment of a female part from the piston end counter to the sliding direction.

A further preferred embodiment of the syringe barrel is characterized in that the piston end is designed to engage with an axial latching element formed at a female part.

A further preferred embodiment of the syringe barrel is characterized in that the piston end is formed to engage with a latching element of a female part, in the form of a protrusion preferably a wedge.

An alternative preferred embodiment of the syringe barrel is characterized in that the piston end of the syringe barrel has a protrusion, designed to engage with a latching element at a female part in the form of an indentation.

A further preferred embodiment of the syringe barrel is characterized in that a wall section of the sleeve at the piston end is moved back axially, wherein this wall section is designed to engage with an axial latching element of a female part.

A further preferred embodiment of the syringe barrel is characterized in that the piston end has a cover plate, wherein the cover plate is designed and arranged so that together with a cover plate formed at a female part, with the exception of a threaded opening of the female part, it forms a substantially enclosed envelope of the piston end and the female part.

A further preferred embodiment of the syringe barrel is characterized in that the cover plate is substantially arranged on a half of a screw syringe relating to the circumferential direction.

A further preferred embodiment of the syringe barrel is characterized in that the cover plate has a section that takes the form of part of a hollow cylindrical section and which is arranged between two wing grips.

A further preferred embodiment of the syringe barrel is characterized in that the abutting surface takes the form of part of the cover plate.

The syringe barrel and its preferred embodiments have features that make them suitable in particular for use as a screw syringe according to the invention and its further developments. Concerning the embodiments, specific features, variants and advantages of the features of the syringe barrel and its further development reference is made to the above description on the corresponding features of the screw syringe.

According to a further aspect of the invention the object is achieved by a female part for a screw syringe for dispensing a material according to any one of the embodiments of the screw syringe described above, comprising an internal thread for engaging with an external thread of a piston spindle, wherein the female part is designed so that it can be slid in a radial sliding direction onto a piston end of a syringe barrel for a screw syringe according to any one of the embodiments of the screw syringe described above, wherein the female part has a flange, which can be brought into a form fit with a counter-surface formed at a piston end of a syringe barrel so that a relative axial displacement between the female part and the syringe barrel in the discharge direction is prevented, the female part has retaining surfaces, that can be brought into a form fit with counter-retaining surfaces formed at a piston end of a syringe barrel so that a relative axial displacement between the female part and the syringe barrel counter to the discharge direction is prevented, and the retaining surfaces can be brought into a form fit with the counter-retaining surfaces so that a relative radial movement between the retaining surfaces and the counter-retaining surfaces, directed perpendicularly to the sliding direction, is prevented.

A preferred embodiment of the female part is characterized in that the retaining surfaces are inclined to the longitudinal axis and/or undercut so that a radial relative movement between the retaining surfaces and corresponding inclined and/or undercut counter-retaining surfaces, directed perpendicularly to the sliding direction, is prevented.

A preferred embodiment of the female part is characterized in that the retaining surfaces have a stepped design so that a radial relative movement between the retaining surfaces and corresponding stepped design counter-retaining surfaces, directed perpendicularly to the sliding direction, is prevented.

A further preferred embodiment of the female part is characterized in that the retaining surfaces can be brought into a form fit with the counter-retaining surfaces so that a spreading apart of the female part or parts thereof outwards due to the force applied by operation of a piston spindle is prevented.

A further preferred embodiment of the female part is characterized in that the retaining surfaces can be brought into a form fit with the counter-retaining surfaces so that upon application of an axial force due to operation of a piston spindle force components act on the retaining surfaces in a direction falling in a plane substantially perpendicular to the sliding direction.

A further preferred embodiment of the female part is characterized in that the piston end has at least one abutting surface, designed and arranged so that with an abutting surface formed at a piston end of a syringe barrel it forms a stop for the female part in the sliding direction.

A further preferred embodiment of the female part is characterized in that the female part has a connection mechanism, which prevents or impedes the detachment of the female part from a piston end of a syringe barrel counter to the sliding direction.

A preferred embodiment of the female part is characterized in that the connection mechanism comprises a flange formed at the female part, having an axial latching element designed to engage with a piston end of a syringe barrel.

A further preferred embodiment of the female part is characterized in that the latching element takes the form of a protrusion, preferably a wedge.

An alternative preferred embodiment of the female part is characterized in that the latching element has an indentation designed to engage with a protrusion formed at a piston end of syringe barrel.

A further preferred embodiment of the female part is characterized in that the latching element is designed to engage with an axially moved back wall section of a sleeve at a piston end of a syringe barrel.

A further preferred embodiment of the female part is characterized in that the female part has a cover plate, designed and arranged so that together with a cover plate formed at a piston end of a syringe barrel, with the exception of a threaded opening, it forms a substantially enclosed envelope of the piston end and the female part.

A further preferred embodiment of the female part is characterized in that the cover plate is substantially arranged on a half of a screw syringe relating to the circumferential direction.

A further preferred embodiment of the female part is characterized in that the cover plate has a section in the form of part of a hollow cylindrical section and which is arranged between two wing grips.

A preferred embodiment of the female part is characterized in that the abutting surface is designed as part of the cover plate.

The female part and its preferred embodiments have features which make them suitable in particular for use for a screw syringe according to the invention and its further developments. Concerning the embodiments, specific features, variants and advantages of the features of the female part and its further developments reference is made to the above description on the corresponding features of the screw syringe.

BRIEF DESCRIPTION OF THE DRAWINGS

A preferred embodiment of the invention is described using the attached Figures. These show as follows:

FIG. 12: a three-dimensional view of the screw syringe according to FIG. 1 with the female part not yet slid on;

DETAILED DESCRIPTION OF THE DRAWINGS

Figure 9:
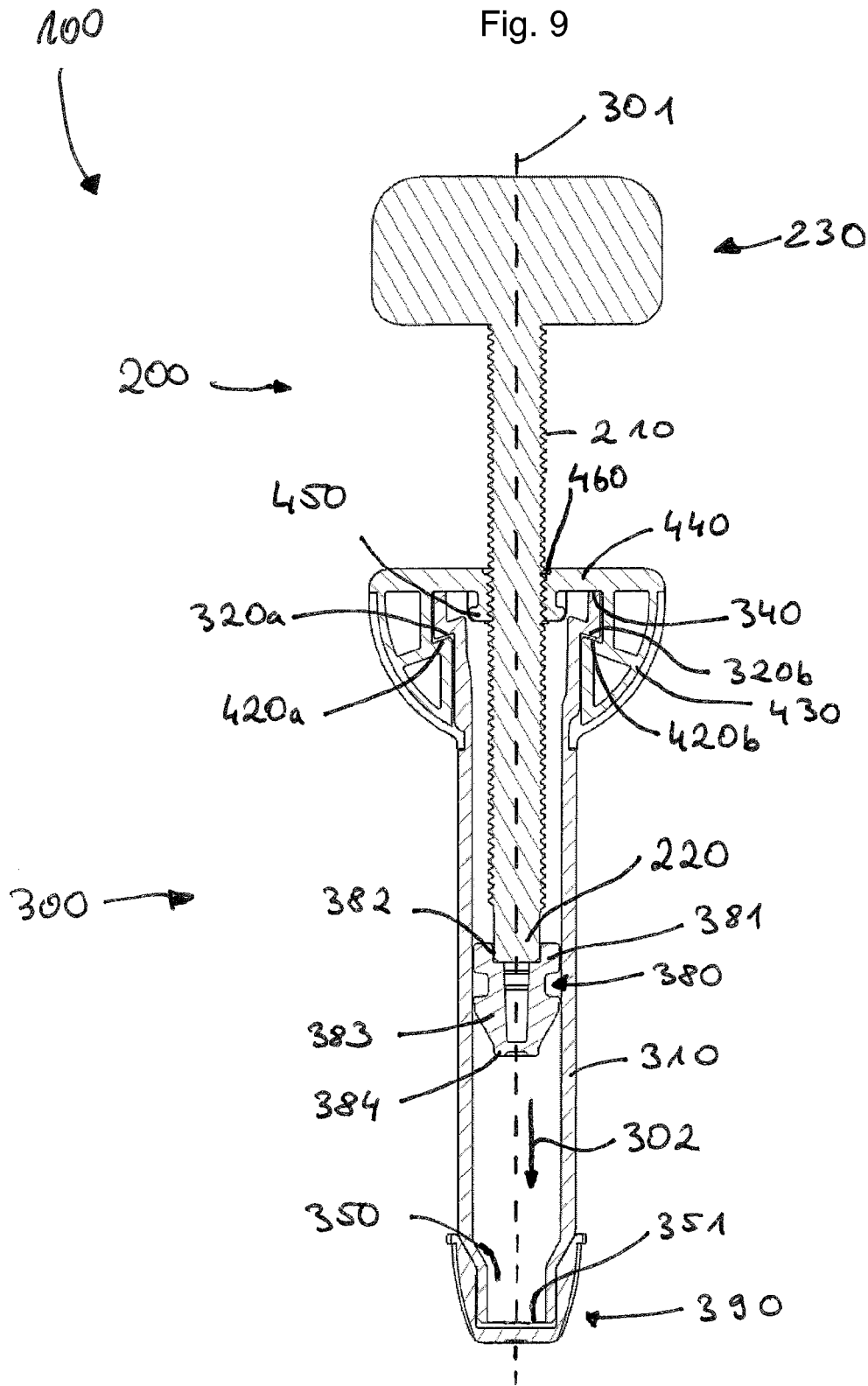
FIG. 9: a longitudinal cross-section along a first sectional plane through the screw syringe according to FIG. 1.
Figure 10:
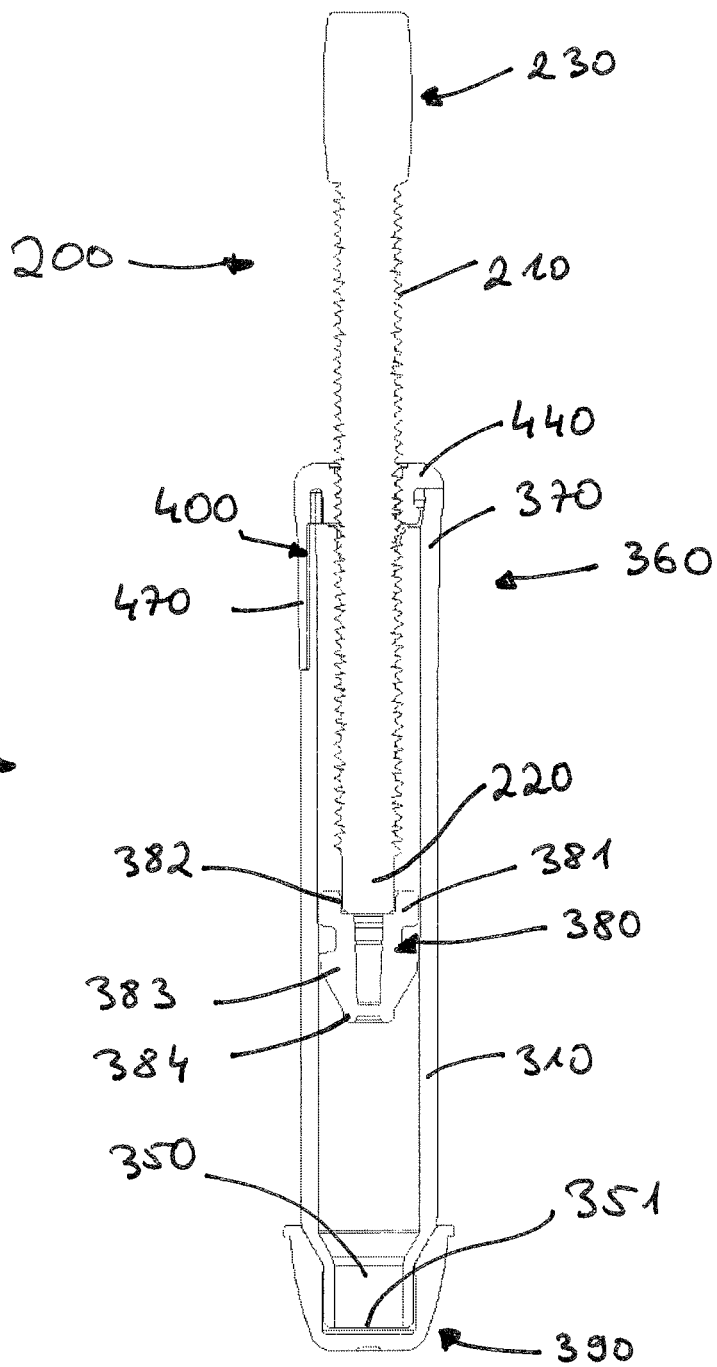
FIG. 10: a longitudinal cross-section along a second sectional plane through the screw syringe according to FIG. 1.
Figure 11:
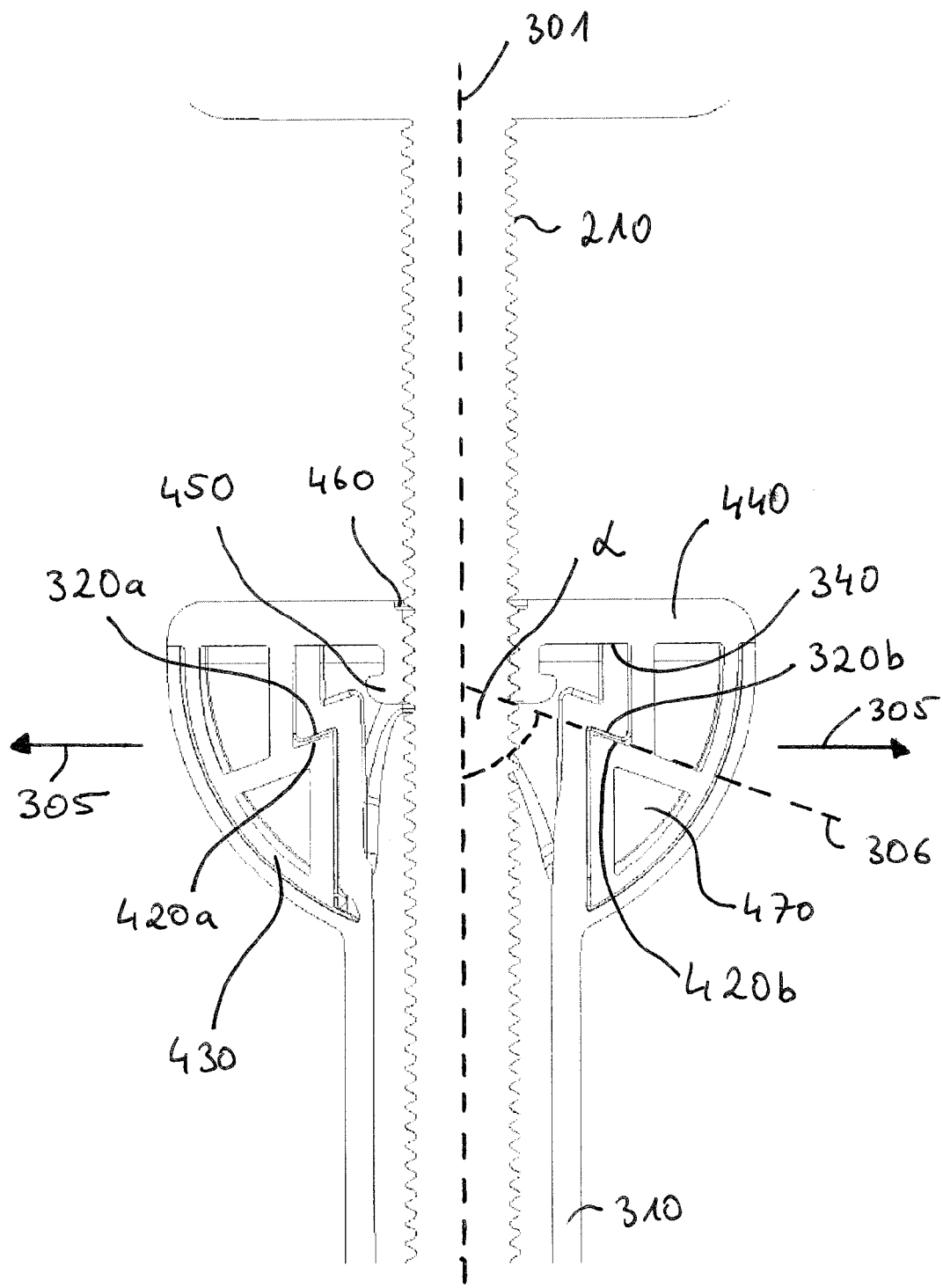
FIG. 11: an enlarged section from FIG. 9 without hatching.
Figure 12:
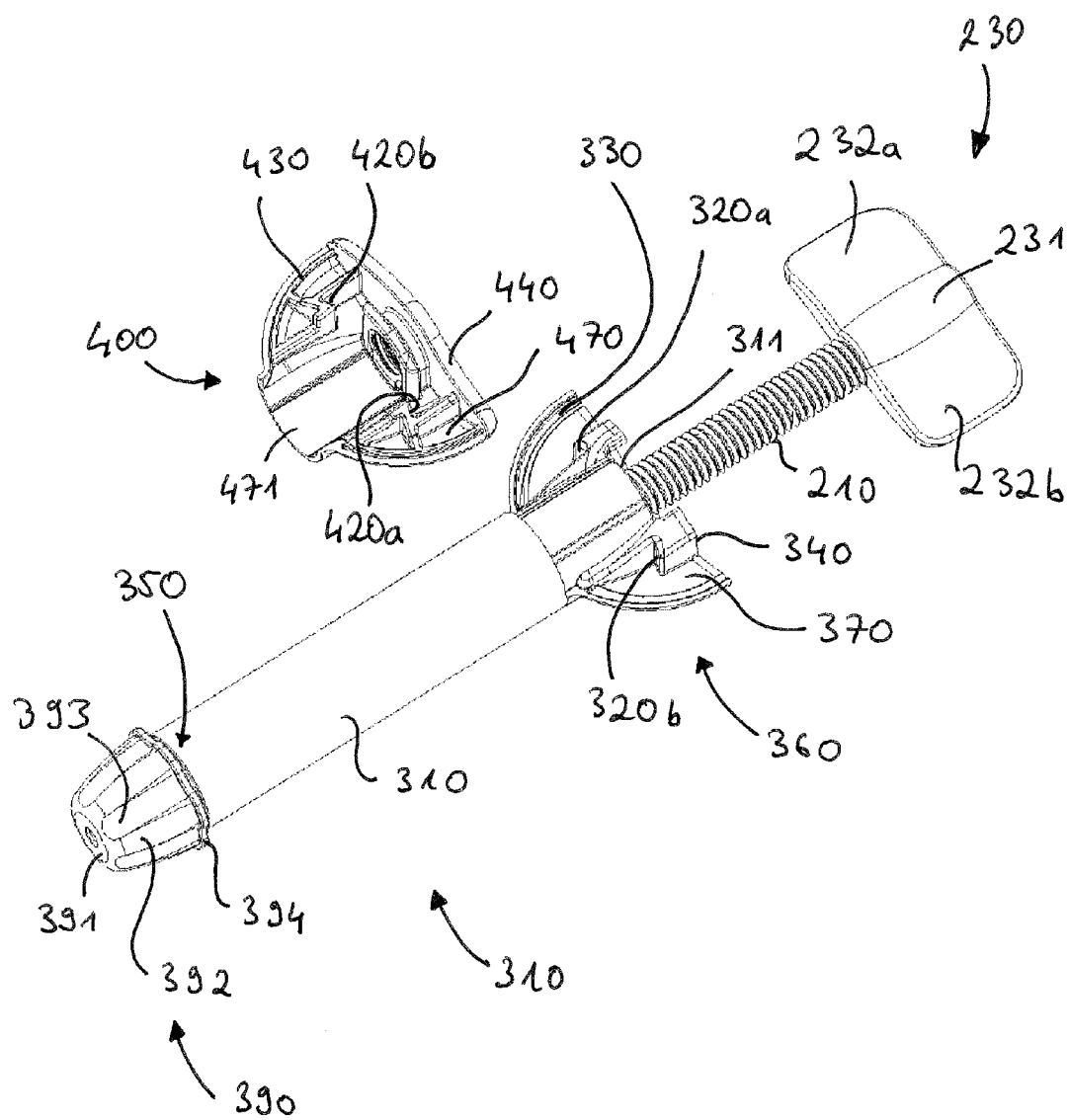
Figure 13:
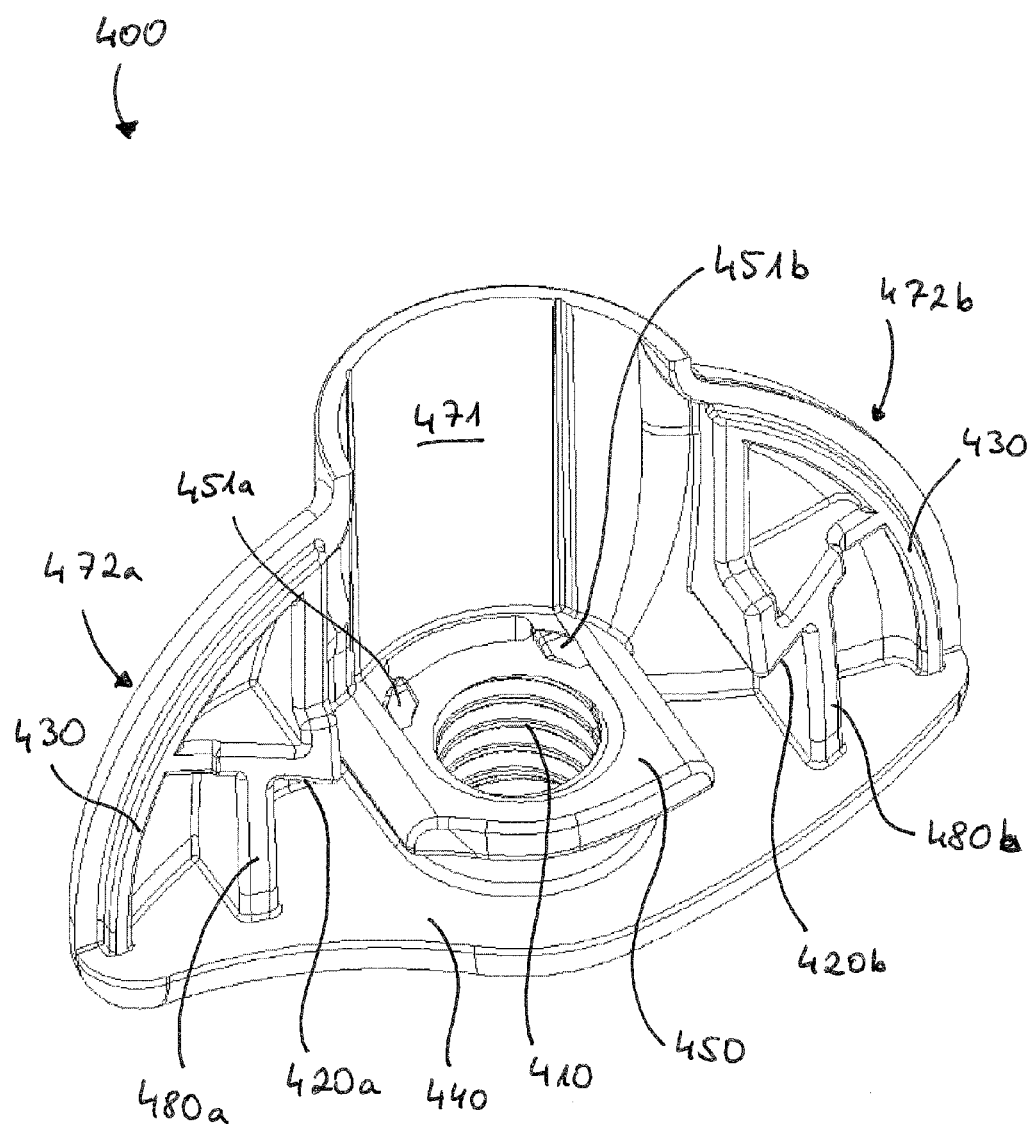
FIG. 13: a three-dimensional view of the female part for the screw syringe according to FIG. 1 and FIG. 14: an enlarged and partially cutaway section from FIG. 5.
Figure 14:
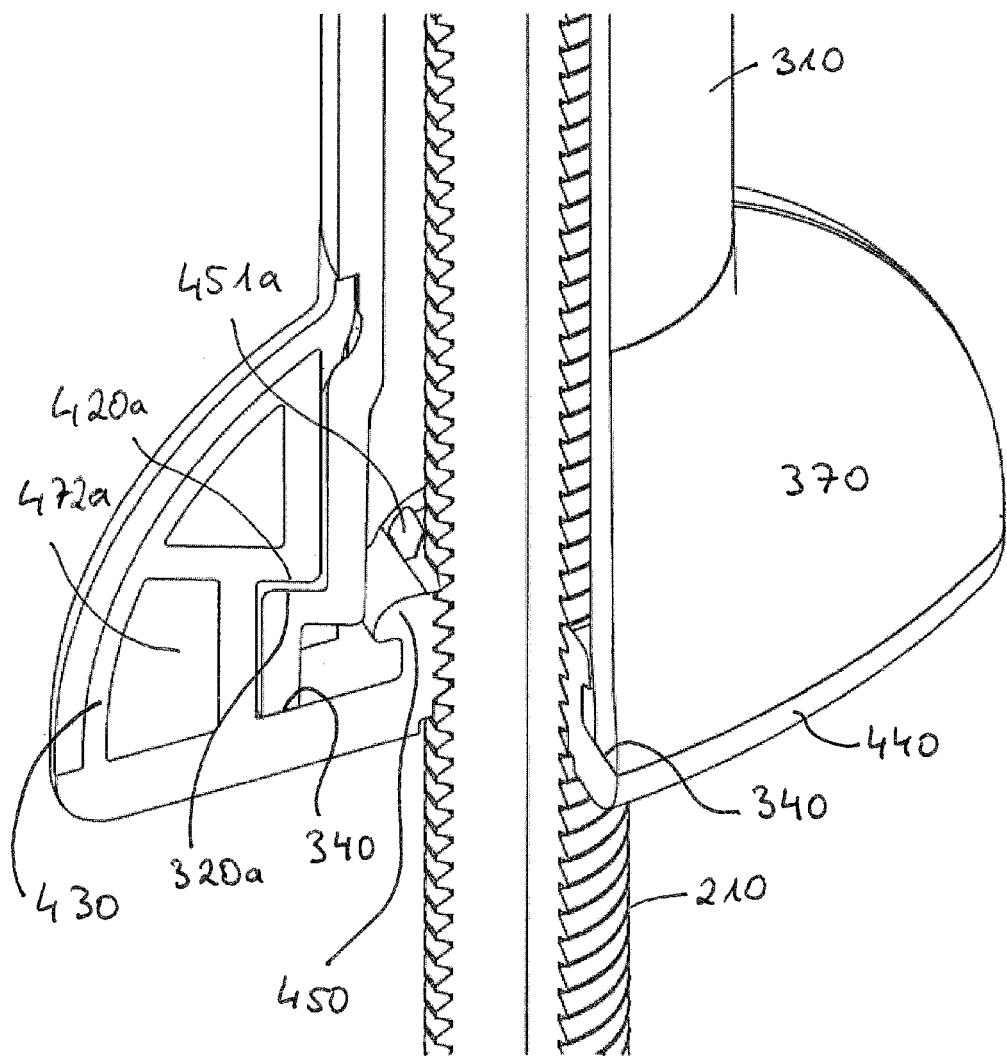

FIGS. 1 through 8 provide views of an example of an embodiment of a screw syringe 100 according to the invention for dispensing a material (not shown), in particular a pasty and/or flowable dental substance. FIGS. 9 through 11 show the screw syringe 100 in cross-sectional views and FIG. 12 shows it in a three-dimensional view with the female part 400 removed, this being shown individually in FIG. 13. Finally, FIG. 14 is a partially cutaway view of a three-dimensional representation of the screw syringe 100.

The screw syringe 100 comprises a piston spindle 200 with an external thread 210, a syringe barrel 300 with a longitudinal axis 301, comprising a sleeve 310 for containing a material (not shown), wherein the sleeve 310 has a discharge end 350 with a discharge opening 351 for dispensing a material contained in the sleeve in an axial discharge direction 302 and a piston end 360 for accommodating the piston spindle 200. The screw syringe 100 also comprises a female part 400 with an internal thread 410 that can in particular be seen in FIG. 13 for engaging with the external thread 210 of the piston spindle 200. The screw syringe 100 also has a cap 390, with which the discharge opening 351 at the discharge end 350 of the syringe barrel 300 can be sealed, which is an advantage in particular in the storage and marketing state of the syringe. The cap 390 has a substantially flat end edge 391 and a flared edge 394 facing the end edge as well as ribs arranged in between, formed by peaks 392 and troughs 393 in between them.

Figure 1:
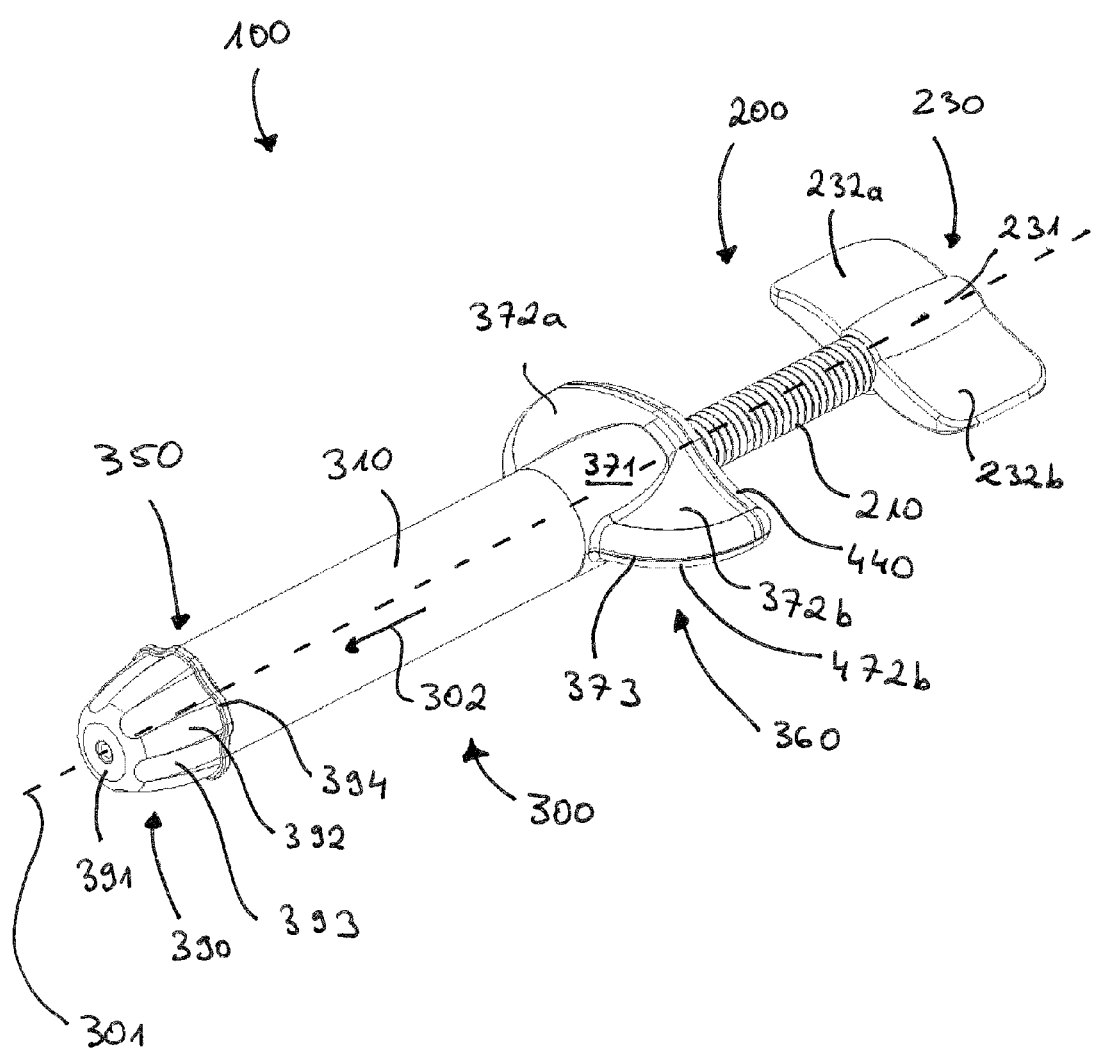
FIG. 1: a three-dimensional view of an example of an embodiment of a screw syringe according to the invention.
Figure 2:
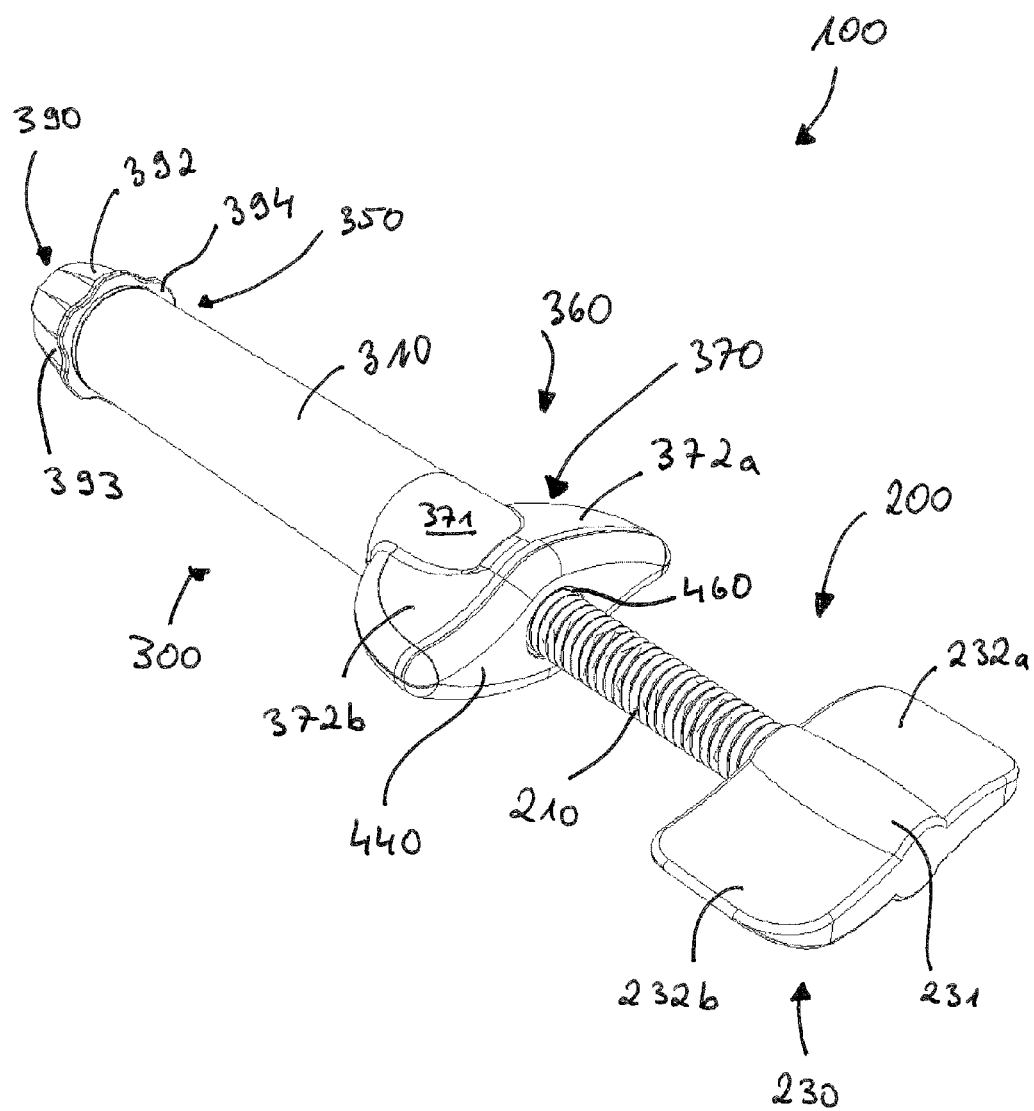
FIG. 2: another three-dimensional view of the screw syringe according to FIG. 1.
Figure 3:
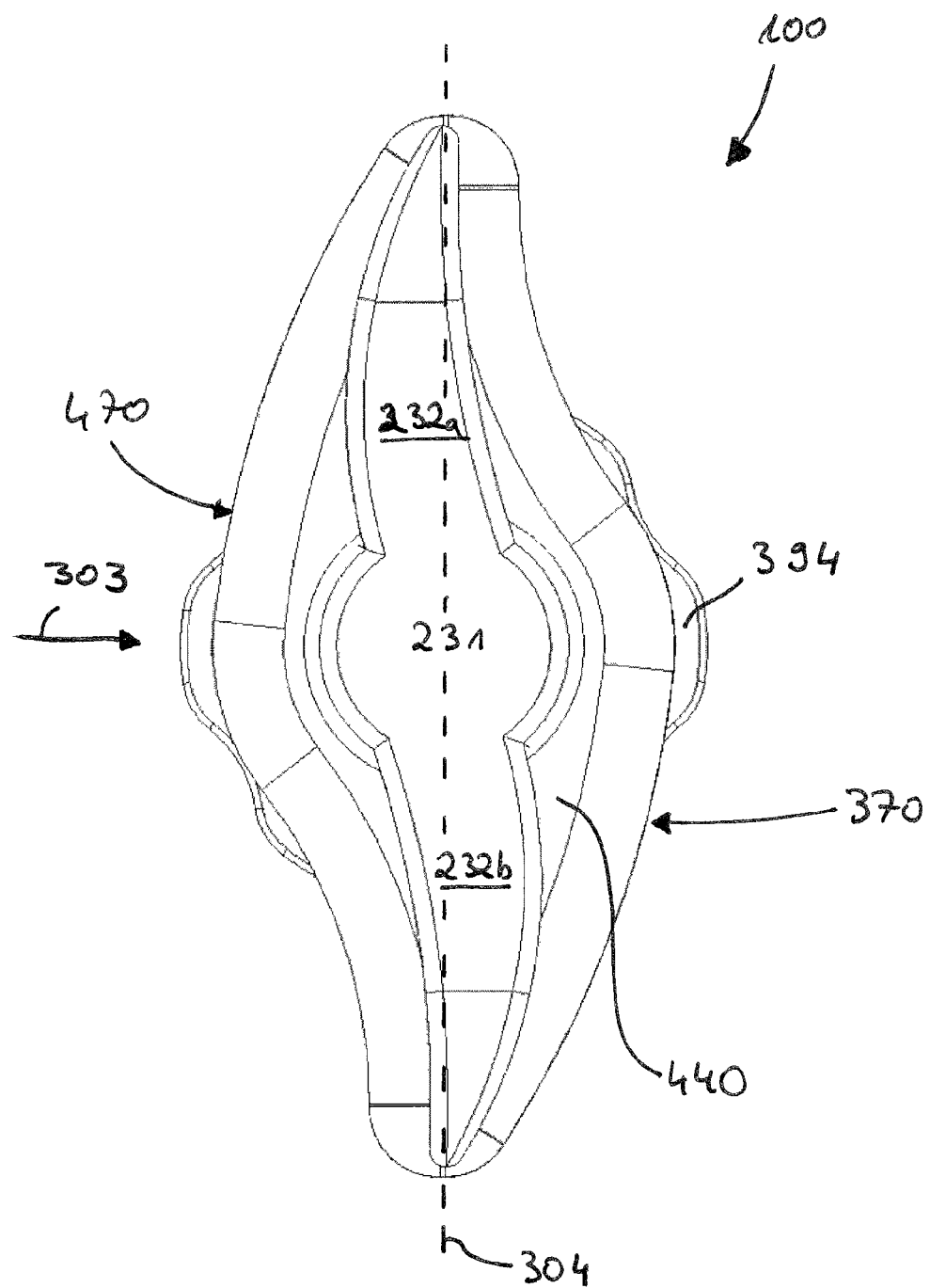
FIG. 3: a top view of the screw syringe according to FIG. 1.
Figure 4:
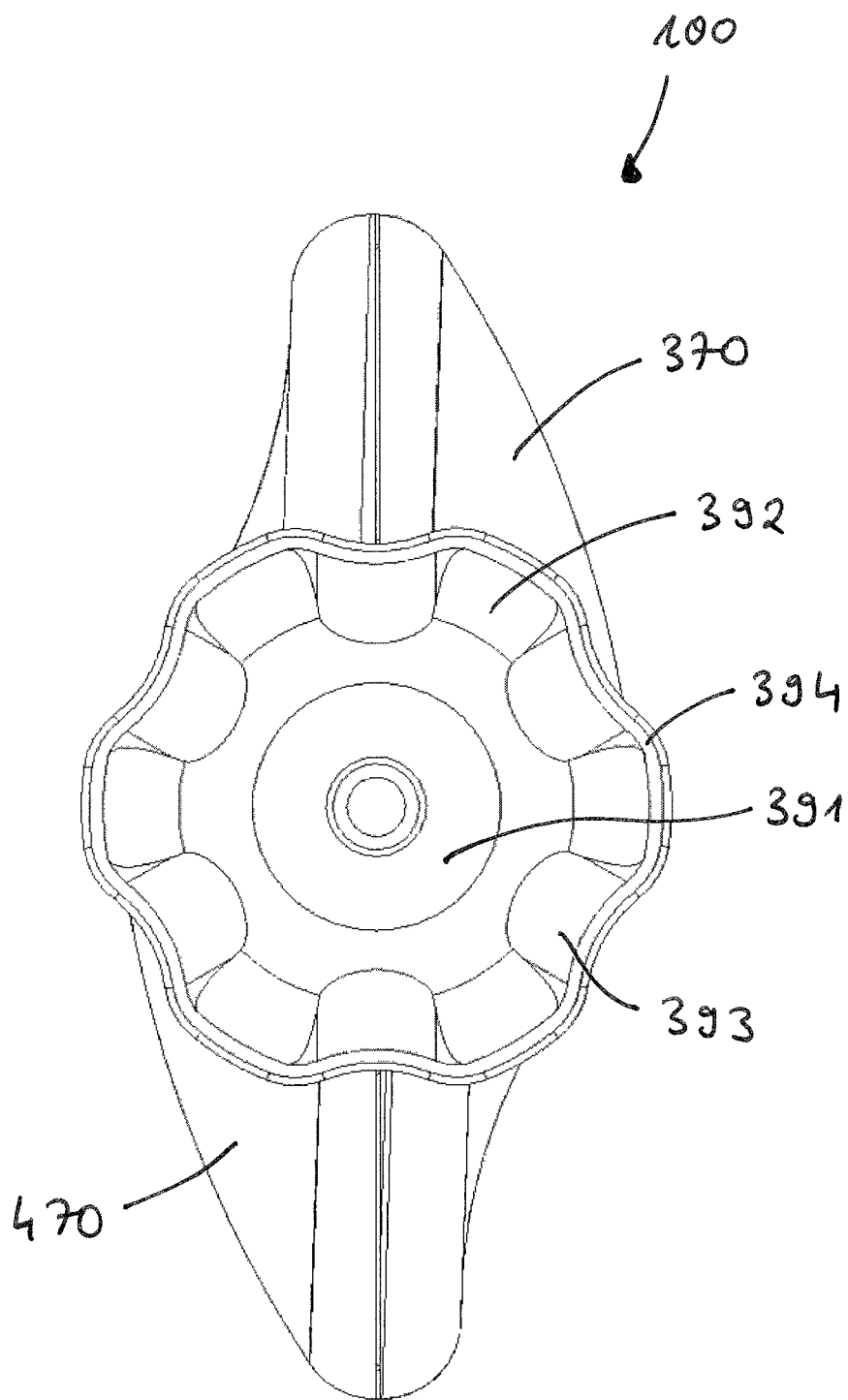
FIG. 4: a bottom view of the screw syringe according to FIG. 1.
Figure 5:
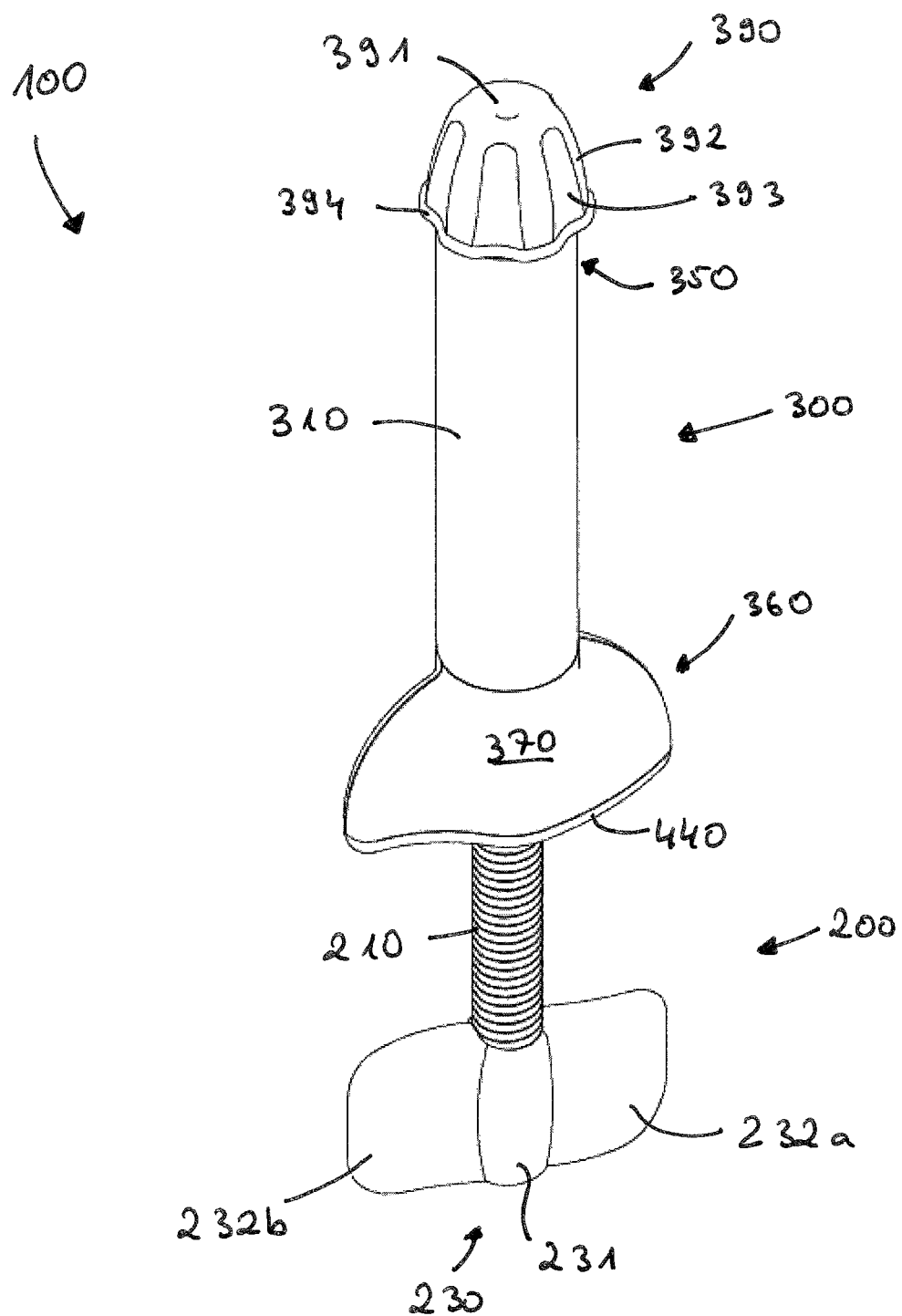
FIG. 5: a further three-dimensional view of the screw syringe according to FIG. 1.
Figure 6:
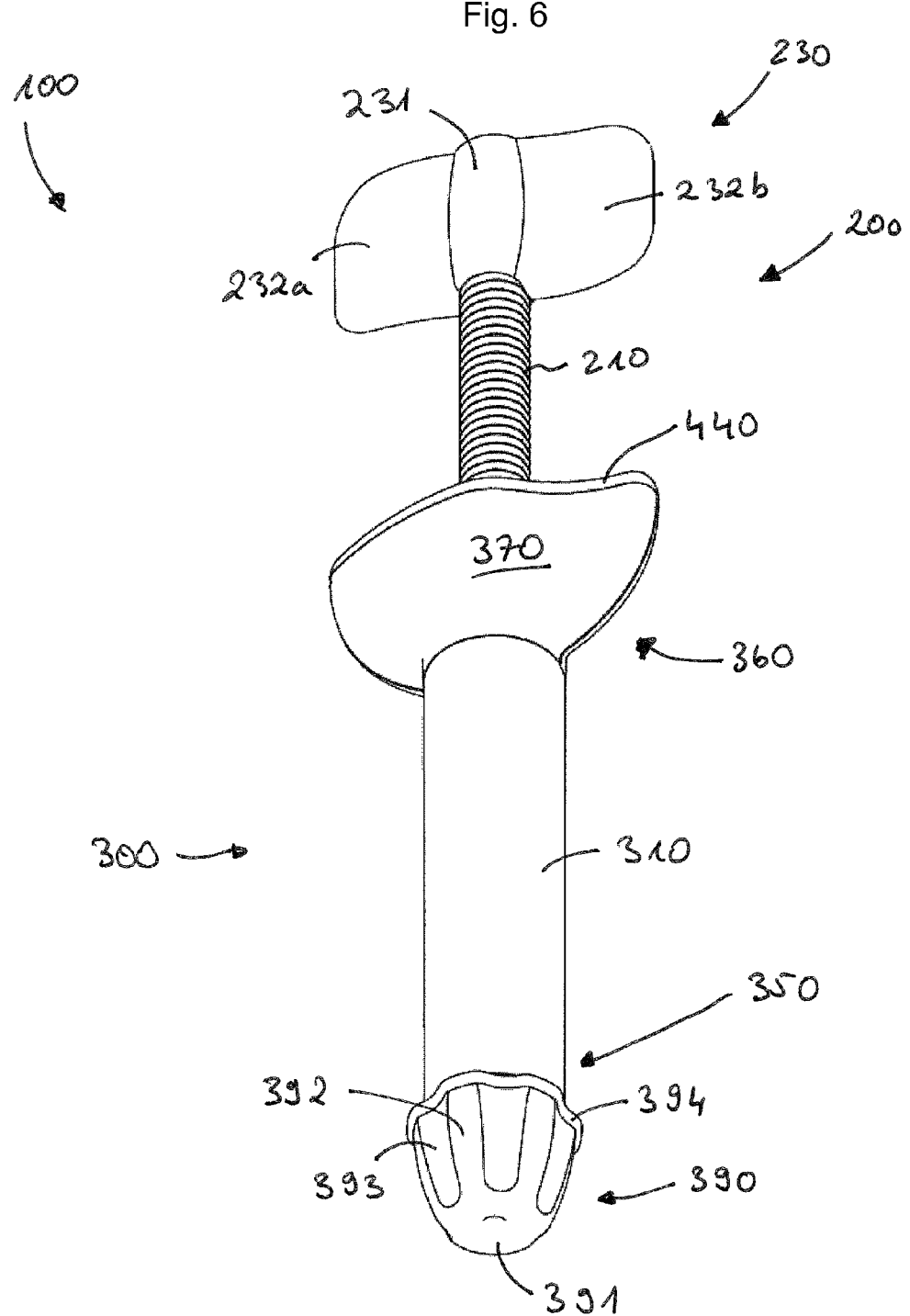
FIG. 6: a further three-dimensional view of the screw syringe according to FIG. 1.
Figure 7:
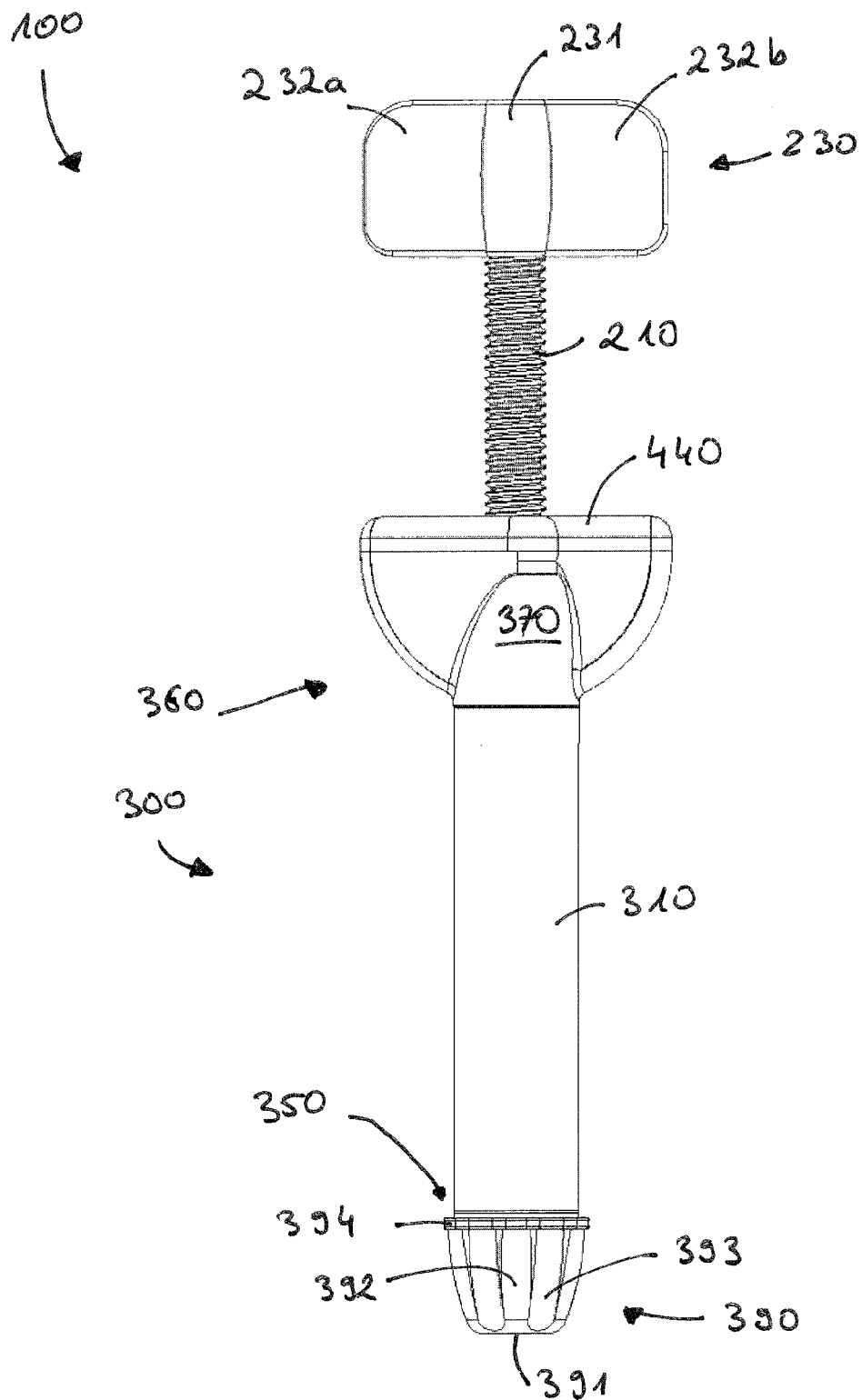
FIG. 7: a further three-dimensional view of the screw syringe according to FIG. 1.
Figure 8:
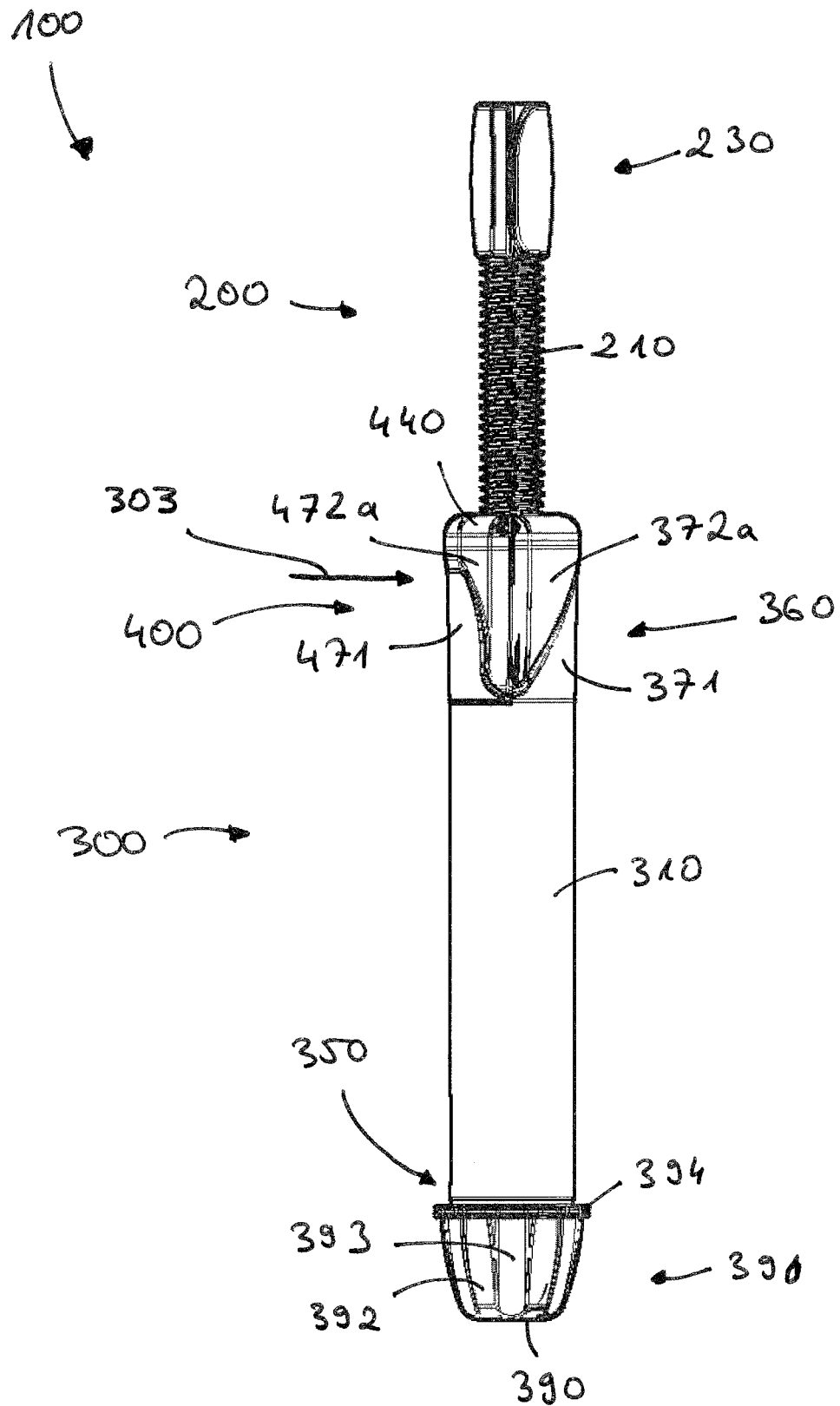
FIG. 8: a side view of the screw syringe according to FIG. 1.

The female part 400 is slid in a radial sliding direction shown in FIGS. 3 and 8 by the arrows 303 onto the piston end 360 of the syringe barrel 300.

The piston spindle has a gripping end 230, which has a partially cylindrical section 231, arranged between two wing grips 232a,b. This gripping section 230 is designed in such a way that the user grips the piston spindle 200 at the gripping section 230 and is able to rotate it in relation to the syringe barrel 300, in order to advance the piston spindle into the sleeve 310.

As can be seen from FIGS. 9 and 10, the screw syringe 100 also has a piston tip 380. The piston tip 380 comprises a first section 381, the external diameter of which is smaller than the internal diameter of the sleeve 310. Alternatively, in particular if the piston tip 380 and the sleeve 310 are formed from elastic plastic, the external diameter of the first section 381 of the piston tip 380 can also be the same size or larger than the internal diameter of the sleeve 310. The first section 381 also has an indentation 382 for engaging with an end 220 of the piston spindle 200. The end 220 of the piston spindle facing the gripping end 230 preferably has no external thread. The piston tip 380 also has a frusto-conical section 383, which at its tapered end 384 has an external diameter that is smaller than the internal diameter of a discharge opening 351 at the discharge end 350. The piston tip 380 serves to occupy the internal cross-section of the sleeve 310, so that with the piston spindle 210, the external diameter of which is preferably smaller than the internal diameter of the sleeve 310, material contained in the sleeve 310 between piston tip 380 and the discharge opening 351 by the advancement of the piston spindle 200 and thus also the piston tip 380 in the sleeve 310 can be expelled through the discharge opening 351.

The syringe barrel 300 at its end facing the discharge end has an area 360, referred to as the piston end. In order to produce the screw syringe 100 the female part 400 is pushed in the radial sliding direction 303 onto the piston end 360.

In the radial direction the abutting surfaces 330 of the piston end 360 and the abutting surfaces 430 of the female part 400 together form a stop, which defines an end position of the female part in relation to the syringe barrel 300, wherein the female part 400 is pushed as far as this end position onto the piston end 360 so that the abutting surfaces 430, 330 come up against each other and further sliding of the female part onto the piston end 360 is not possible. In this end position the internal thread 410 of the female part 400 and the sleeve 310 of the syringe barrel 300 are preferably coaxially aligned.

The section 471 can alternatively or additionally be used as the abutting surface.

The piston end 360 has a cover plate 370, on which the abutting surface 330 of the piston end 360 is formed. The female part 400 likewise has a cover plate 470, on which the abutting surface 430 is formed. The cover plates 370, 470 are substantially arranged in the halves facing in the circumferential direction of the screw syringe 100, meaning that the cover plate 370 is located substantially in a half of a plane 304, containing the longitudinal axis 301, facing a cover plate 470 of the female part and preferably arranged perpendicularly to the sliding direction 303, as can be seen in particular in FIG. 3. The cover plates 370, 470 in each case have a section 371, 471, which takes the form of part of a hollow cylindrical section and which in each case is arranged between two wing grips 372a,b, 472a,b. In the ready-to-use state of the screw syringe 100 with the female part 400 slid onto the piston end 360 the cover plates 370, 470 together, with the exception of a threaded opening 460 of the female part 400, substantially form a enclosed envelope of the piston end 360 and the female part 400. Here the cover plates 370, 470 are designed and arranged in such a way that a gap 373 between the female part 400 and the end 360 is arranged between the edges of the wing grips 372a,b, 472a,b, so that when the screw syringe is operated and when the wing grips are gripped by a user the gap 373 does not have to be touched as a priority, so that the danger of contamination of the screw syringe and in particular the gap 373 can be reduced.

Furthermore by gripping with the fingers the user will push the abutting surfaces 430 of the female part 400 against the abutting surfaces 330.

The female part 400 has a flange 440, which once the female part 400 has been slid onto the piston end 360 creates a form fit with the counter-surface 340 of the piston end 360 so that an axial displacement of the female part 400 in relation to the syringe barrel 300 in the discharge direction 302 is prevented. The female part 400 also has a pair of retaining surfaces 420a,b, which create a form fit with a pair of counter-retaining surfaces 320a,b of the piston end 360 once the female part 400 has been slid onto the piston end 360 so that an axial displacement of the female part 400 in relation to the syringe barrel 300 counter to the discharge direction 302 is prevented. In this way once it has been slid on the female part 400 is secured in the axial direction in relation to the syringe barrel 300. The retaining surfaces 420a,b of the female part 400 can preferably be formed on a pair of arms 480a,b pointing outwards in the axial direction from the flange 440 of the female part.

The retaining surfaces 420a,b of the female part 400 and the counter-retaining surfaces 320a,b of the piston end 360 are also brought into a form fit, so that a radial relative movement, directed perpendicularly to the sliding direction 303, between the retaining surfaces 420a,b and the counter-retaining surfaces 320a,b is prevented. In the embodiment shown here by way of example the form fit is created by an undercut formed by an inclining of the retaining surfaces 420a,b and the counter-retaining surfaces 320a,b in relation to the longitudinal axis 301. The retaining surfaces 420a,b and counter-retaining surfaces 320a,b are inclined at an angle of 70° to the longitudinal axis 301, which is shown in FIG. 11 by the angle alpha between the plane identified as 306 of the retaining surfaces 420b and the counter-retaining surfaces 320b and the longitudinal axis 306.

In this way a spreading apart of the female part 400 or of the arms 480a,b with the retaining surfaces 420a,b formed thereon outward in the direction of the arrows identified in FIG. 11 as 305 is prevented, if an axial force is applied during operation of the piston spindle. The retaining surfaces 420a,b and the counter-retaining surfaces 320a,b are inclined in relation to the longitudinal axis 301 or undercut, so that if such axial force is applied by operation of the piston spindle 200 at the retaining surfaces 420a,b and the counter-retaining surfaces 320a,b force components operate in a direction falling in planes that are substantially perpendicular to the sliding direction 303. These force components operate in particular substantially perpendicularly to the sliding direction 303 and substantially perpendicularly to the longitudinal axis 301, so that an outward movement of the retaining surfaces 420a,b of the female part in the direction of the arrows 305 is prevented or at least impeded.

The piston end 360 and the female part 400 also have a connection mechanism, which prevents or at least impedes a detachment of the female part 400 from the piston end 360 counter to the sliding direction 303 so that when the screw syringe is handled correctly with light to normal exertion of force by a user the female part 400 cannot be detached from the piston end 360. The connection mechanism according to the invention must not prevent detachment with greater exertion of force.

The connection mechanism comprises a flange 450 formed at the female part 400, having two axial latching elements, in the form of wedge-shaped protrusions 451a,b. These wedge-shaped protrusions 451a,b protrude in the axial direction beyond the flange 450 and as a result of their extension in the axial direction are also referred to as axial latching elements. Alternatively (not shown) a latching element can also take the form of an indentation pointing in the axial direction.

As can be seen in particular in FIG. 12, a wall section 311 of the sleeve 310 is moved back axially on the piston end 360. As can also be seen from FIG. 12, the wall section 311 takes the form of part of a hollow cylindrical section. When the female part 400 is slid onto the piston end 360 the axially moved back wall section slides over the axial latching elements 451a,b on the flange 450 of female part 400 in the form of wedge-shaped protrusions and latches behind the latching elements 451a,b creating a latched or snap connection between the female part 400 and piston end 360, if the female part 400 upon impact between the abutting surfaces 330, 430 has reached its end position. In this way it is possible to prevent the female part 400 dropping off the syringe barrel 300 or being easily detached counter to the sliding direction 302.

The axially moved back wall section 311 also allows a relatively long internal thread 410 in the female part 400, without the flange 440 having to be designed with a very thick wall over its entire extension and without requiring an extension protruding in the direction of the gripping end 230 of the spindle.

The external diameter of the piston spindle 200, in particular of the external thread 210, and the internal diameter of the sleeve 310 or of the sections 371, 471 of the cover plates 370, 470 and the wall sections 311 are matched to each other here so that the latching elements 451a,b can be arranged in the space between the piston spindle and the inner wall of the sleeve 310 or the sections 471, 371 of the cover plates and the wall section 311, as shown in particular in FIG. 14.

The syringe barrel 300, female part 400, piston spindle 200, piston tip 380 and cap 390 are preferably produced by injection molding, in each case as single plastic parts, wherein the sleeve 310 of the syringe barrel 300 is filled with the material to be dispensed. The parts of the piston spindle 200, syringe barrel 300, female part 400, piston tip 380 and cap 390 are assembled into a ready-to-use screw syringe 100. Here the piston tip 380 is introduced from the piston end 360 side into the sleeve, the female part 400 is slid in the radial sliding direction 303 onto the piston end 360 of the syringe barrel 300 and the piston spindle 200 with its external thread 210 is screwed into the internal thread 410 of the female part 400. When the female part 400 is slid onto the piston end 360 the piston spindle 200 is preferably not yet introduced into the sleeve 310 of the syringe barrel 300. The cap 390 is preferably attached in a removable fashion on the discharge end 350.

In order to produce a ready-to-use screw syringe 100 according to the invention the sliding of the female part 400 onto the piston end 360 of the syringe barrel 300 is in particular of importance. To do this the female part 400 shown in FIGS. 12 and 13 is pushed on to the piston end 360 of the syringe barrel 300 in the radial sliding direction 303. Here the female part 400 is positioned on the piston end 360 in such a way that initially the edges of the flanges 440 and 450 and the retaining surfaces 420a,b come into contact with the corresponding edges of the counter-surface 340, of the axially moved back wall section 311 and the counter-retaining surfaces 320a,b. With further pushing or pressing of the female part 400 onto the piston end 360 the respective surface pairings—flange 440 and counter-surface 340, retaining surfaces 420a,b and counter-retaining surfaces 320a,b and flange 450 and wall section 311—slide along each other. Shortly before reaching the end position of the female part by impacting the abutting surfaces 330, 430, the axially moved back wall section 311 slides over the latching elements 451a,b of the flange 450 of the female part 400 in the form of wedge-shaped protrusions and latches in the end position behind the wedge-shaped protrusions 451a,b. In this end position the preferably somewhat arched abutting surfaces 330, 430 preferably substantially come into full surface contact with one another and the axially moved back wall section 311 is arranged between the axial latching elements 451a,b and the section 471 in the form of part of a hollow cylinder of the cover plate 470. In the end position the retaining surfaces 420a,b and counter-retaining surfaces 320a,b are likewise preferably substantially in full surface contact with one another. The counter-surface 340 is in contact with the side of the flange 440 of the female part 400 turned towards the flange 450.

The invention claimed is:

1. A screw syringe (100) for dispensing a material, in particular a pasty and/or flowable dental substance, comprising
    a piston spindle (200) with an external thread (210);
    a syringe barrel (300) with a longitudinal axis (301), comprising a sleeve (310) for containing a material, wherein the sleeve has a discharge end (350) for discharging a material contained in the sleeve in an axial discharge direction (302) and a piston end (360) for accommodating the piston spindle (200), and
    a female part (400) with an internal thread (410) for engaging with the external thread (210) of the piston spindle (200),
    wherein the female part (400) is slid in a radial sliding direction (303) onto the piston end (360) of the syringe barrel (300),
wherein
    the female part (400) has a flange (440), which creates a form fit with a counter-surface (340) on the piston end (360) so that an axial displacement of the female part (400) in relation to the syringe barrel (300) in the discharge direction (302) is prevented;
    the female part (400) has retaining surfaces (420a,b), which create a form fit with counter-retaining surfaces (320a,b) of the piston end (360) so that an axial displacement of the female part (400) in relation to the syringe barrel (300) counter to the discharge direction (302) is prevented, and
    the retaining surfaces (420a,b) and counter-retaining surfaces (320a,b) create a form fit, so that a radial relative movement between the retaining surfaces and the counter-retaining surfaces, directed perpendicularly to the sliding direction, is prevented, wherein the retaining surfaces (420a,b) and counter-retaining surfaces (320a,b) form an angle ranging from 5 to 85° relative to the longitudinal axis (301).

2. The screw syringe (100) as claimed in claim 1, wherein the retaining surfaces (420a,b) and counter-retaining surfaces (320a,b) are inclined such that the radial relative movement between the retaining surfaces (420a,b) and the counter-retaining surfaces (320a,b), directed perpendicularly to the radial sliding direction (303), is prevented.

3. The screw syringe (100) as claimed in claim 1, wherein the retaining surfaces (420a,b) and counter-retaining surfaces (320a,b) have a stepped design so that the radial relative movement between the retaining surfaces (420a,b) and the counter-retaining surfaces (320a,b), directed perpendicularly to the radial sliding direction (303), is prevented.

4. The screw syringe (100) as claimed in claim 1, wherein the retaining surfaces (420a,b) and counter-retaining surfaces (320a,b) create the form fit so that spreading apart of the female part (400) outwards due to the force applied by operation of the piston spindle (200) is prevented.

5. The screw syringe (100) as claimed in claim 1, wherein the retaining surfaces (420a,b) and counter-retaining surfaces (320a,b) create the form fit so that when an axial force is applied by operation of the piston spindle (200) on the retaining surfaces (420a,b) and counter-retaining surfaces (320a,b) force components operate in a direction falling in a plane substantially perpendicular to the radial sliding direction (303).

6. The screw syringe (100) as claimed in claim 1, wherein the piston end (360) and the female part (400) each have at least one abutting surface (330, 430) adapted to form a stop for the female part in the radial sliding direction (303).

7. The screw syringe (100) as claimed in claim 6, wherein the abutting surfaces (330, 430) are in the form of part of cover plates (370, 470).

8. The screw syringe (100) as claimed in claim 1, wherein the piston end (360) and/or the female part (400) has a connection mechanism, that prevents or impedes a detachment of the female part (400) from the piston end (360) counter to the radial sliding direction (303).

9. The screw syringe (100) as claimed in claim 8, wherein the connection mechanism comprises a flange (450) formed at the female part (400), having an axial latching element (451a,b), that engages with the piston end (360).

10. The screw syringe (100) as claimed in claim 9, wherein the latching element has an indentation that engages with a protrusion formed on the piston end of the syringe barrel.

11. The screw syringe (100) as claimed in claim 9, wherein when a wall section (311) of the sleeve (310) on the piston end (360) is moved axially back from the discharge end (350) the wall section (311) engages with the latching element (451*a,b*) of the female part (400).

12. The screw syringe (100) as claimed in claim 8, wherein a latching element (451*a,b*) is in the form of a protrusion, preferably a wedge.

13. The screw syringe (100) as claimed in claim 1, wherein the piston end (360) and the female part (400) each have a cover plate (370, 470), wherein the cover plates (370, 470) are designed and arranged to form a substantially enclosed, with the exception of a threaded opening (460) of the female part (400), envelope of the piston end (360) and the female part (400).

14. The screw syringe (100) as claimed in claim 13, wherein the cover plates (370, 470) are substantially arranged in halves of the screw syringe (100) facing each other in a circumferential direction.

15. The screw syringe (100) as claimed in claim 13, wherein the cover plates (370, 470) each have a section forming part of a hollow cylindrical section (371, 471), and are arranged between two wing grips (372*a,b*, 472*a,b*).

16. The screw syringe (100) as claimed in claim 13, wherein abutting surfaces (330, 430) form part of the cover plates (370, 470).

17. The screw syringe (100) as claimed in claim 1, characterized by a piston tip (380) arranged in the syringe barrel (300) comprising a first section (381), the external diameter of which is matched to an internal diameter of the sleeve (310).

18. The screw syringe as claimed in claim 17, wherein
(a) the first section (381) of the piston tip has an indentation (382) for engaging with an end (220) of the piston spindle (200); or
(b) the piston tip (380) comprises a frusto-conical section (383), which at its tapered end (384) has an external diameter that is smaller than the internal diameter of a discharge opening (351) at the discharge end (350); or
(c) both (a) and (b).

* * * * *